US008017651B2

(12) United States Patent
Pacioretty et al.

(10) Patent No.: US 8,017,651 B2
(45) Date of Patent: *Sep. 13, 2011

(54) COMPOSITIONS AND METHODS FOR THE TREATMENT OF HIV-ASSOCIATED FAT MALDISTRIBUTION AND HYPERLIPIDEMIA

(75) Inventors: Linda M. Pacioretty, Brooktondale, NY (US); John G. Babish, Brooktondale, NY (US)

(73) Assignee: Bionexus, Ltd., Ithaca, NY (US)

( * ) Notice: Subject to any disclaimer, the term of this patent is extended or adjusted under 35 U.S.C. 154(b) by 1208 days.

This patent is subject to a terminal disclaimer.

(21) Appl. No.: 10/699,195

(22) Filed: Oct. 31, 2003

(65) Prior Publication Data

US 2004/0106591 A1    Jun. 3, 2004

Related U.S. Application Data

(60) Provisional application No. 60/428,246, filed on Nov. 22, 2002.

(51) Int. Cl.
*A01N 37/00* (2006.01)
*A01N 37/18* (2006.01)
*A61K 31/19* (2006.01)
*A61K 31/20* (2006.01)
*A61K 31/16* (2006.01)
*A61K 31/095* (2006.01)

(52) U.S. Cl. ........ 514/557; 514/558; 514/613; 514/625; 514/706

(58) Field of Classification Search .................. 514/184, 514/557, 558, 613, 625, 706; 435/6, 8
See application file for complete search history.

(56) References Cited

U.S. PATENT DOCUMENTS 5,750,351 A * 5/1998 Medford et al. ............. 435/7.21
2002/0132219 A1 * 9/2002 McCleary ..................... 435/1.1

* cited by examiner

*Primary Examiner* — Yong Chong

(57) ABSTRACT

Compositions for treating or preventing fat maldistribution or hyperlipidemia resulting from anti-retroviral treatment of HIV-1 infection are disclosed. The compositions contain a conjugated fatty acid or alcohol and at least one member selected from the group consisting of a thiol-containing compound and a bioavailable form of trivalent chromium. Methods of treating a subject suffering from HIV-associated fat maldistribution or hyperlipidemia by administering a composition that includes a conjugated fatty acid or conjugated fatty alcohol and at least one member selected from the group consisting of a thiol-containing compound and a bioavailable form of trivalent chromium are similarly provided.

2 Claims, No Drawings

US 8,017,651 B2

COMPOSITIONS AND METHODS FOR THE TREATMENT OF HIV-ASSOCIATED FAT MALDISTRIBUTION AND HYPERLIPIDEMIA

RELATED APPLICATIONS AND PRIORITY CLAIM

This application claims priority to U.S. Provisional Patent Application Ser. No. 60/428,246, filed Nov. 22, 2002, the entirety of which is incorporated herein by reference.

BACKGROUND OF THE INVENTION

1. Field of the Invention

The present invention relates generally to nutritional or pharmaceutical compositions and methods of use for the treatment of HIV-associated fat maldistribution and hyperlipidemia.

2. Description of the Related Art

As in the case with many other infections, HIV infection is accompanied by disturbances in lipid and glucose metabolism. These metabolic abnormalities are further confounded by hypercholesterolemia and hypertriglyceridemia induced by anti-retroviral (AR) drugs. It has been estimated that almost two-thirds of HIV/AIDS patients exhibit abnormal fat distribution coincident with AR-therapy (ART). Clinicians have termed this abnormal fat distribution lipodystrophy or fat maldistribution. Although various terms have been used, the term both lipodystrophy and fat maldistribution will be used here interchangeably to describe the syndrome of body shape changes related to changes in fat distribution in people with HIV/AIDS receiving AR-therapy (HIV/ART).

Various descriptions have been proposed for the morphologic abnormalities and the metabolic alterations that appear to be associated with fat maldistribution. While clinicians have a general understanding of changes in fat distribution occurring in persons with HIV, no consensus exists among them on the clinical measures used to define fat maldistribution. When questioned, physicians generally describe a syndrome of "maldistribution of body fat," "buffalo hump," "thinning of arms and legs," "facial thinning," and/or "increases in abdomen size." Few physicians mention metabolic markers when defining fat maldistribution.

"Lipo" refers to fat and "dystrophy" means abnormal growth. Before being recognized in HIV-infected patients, the lipodystrophies were described as rare abnormalities of adipose tissue characterized by body shape changes and metabolic abnormalities, including insulin resistance, hyperglycemia, and hyperlipidemia.

Although there appear to be some similarities between the established lipodystrophies seen prior to HIV and that seen in HIV/ART patients, there is little evidence of fat accumulation or maldistribution as being a common presentation in persons with lipodystrophy before the development of successful ART combinations for HIV. The fat maldistribution with HIV/AR-related lipodystrophy is typically a mix of central fat accumulation and peripheral fat loss, and this pattern does not seem to fit readily into any definition of previously described lipodystrophies.

Historically, before HIV, lipodystrophy was used to describe features of lipoatrophy only. The use of this term to describe features of fat accumulation as well as fat loss in HIV/ART-patients helped to initiate the confusion, which still exists, on the clinical case definition of HIV/ART-related lipostrophy. Nevertheless, it is now accepted that the lipodystrophy seen in patients with HIV infection receiving ART is a syndrome involving physical and metabolic abnormalities.

The physical changes associated with the HIV/ART lipodystrophy syndrome can be divided into two major types, both of which involve an abnormal or maldistribution of body fat: lipoatrophy or fat wasting and lipohypertrophy or fat accumulation. An increase in abdominal girth is a common complaint in patients, while thinning of the extremities is also frequently seen, often with prominence of the veins in the arms and legs (cabling) due to subcutaneous fat loss. A substantial proportion of patients report increased wrinkling of the skin with a loss of subcutaneous tissue in the cheeks and around the nose and lips.

Abnormal metabolic changes include altered lipid metabolism manifest by increased triglycerides, increased total cholesterol and increased low-density lipoprotein (LDL) cholesterol. Alterations in glucose metabolism with lipodystrophy include insulin resistance, impaired glucose tolerance and type 2 diabetes.

Although surgery is sometimes elected to remove unsightly fat deposits and restore normal facial appearance, the most frequently prescribed drugs for maintaining normal body composition are recombinant human growth hormone (Somatotrophin®) and anabolic steroids (e.g. Oxandrin®). Other adjunctive measures, such as progressive resistance exercises may also be utilized. Cosmetic surgery appears to be only a stopgap measure and patients frequently continue abnormal body fat deposition. The medications described are highly effective in many patient groups. However, human growth hormone is costly and anabolic steroids may present significant hepatic and cardiovascular risk to the HIV patient.

Among the dietary supplements sold to promote body composition changes, N-acetylcysteine (NAC), L-carnitine, acetyl-L-carnitine, arginine and omega-3 fatty acids have been suggested for wasting and lipodystrophy in HIV/AIDS. No positive data have yet been developed to support these recommendations.

The role of NAC in HIV has been examined since 1989 in 16 peer-reviewed publications (Breitkreutz R, et al. *Improvement of immune functions in HIV infection by sulfur supplementation: two randomized trials* [see comments]. J Mol Med 2000; 78(1):55-62; Akerlund B, et al. *N-acetylcysteine treatment and the risk of toxic reactions to trimethoprim-sulphamethoxazole in primary Pneumocystis carinii prophylaxis in HIV-infected patients*. J Infect 1997; 35:143-147; Jahoor F, et al. *Erythrocyte glutathione deficiency in symptom-free HIV infection is associated with decreased synthesis rate*. Am J Physiol 1999; 276:E205-E211; Walmsley S L, et al. *A randomized trial of N-acetylcysteine for prevention of trimethoprim-sulfamethoxazole hypersensitivity reactions in Pneumocystis carinii pneumonia prophylaxis (CTN 057).* Canadian HIV Trials Network 057 Study Group. J Acquir Immune Defic Syndr Hum Retrovirol 1998; 19(5):498-505; Look M P, et al. *Sodium selenite and N-acetylcysteine in antiretroviral-naive HIV-1-infected patients: a randomized, controlled pilot study*. Eur J Clin Invest 1998; 28:389-397; Herzenberg L A, et al. *Glutathione deficiency is associated with impaired survival in HIV disease*. Proc Natl Acad Sci USA 1997; 94:1967-1972; Akerlund B, et al. *Effect of N-acetylcysteine(NAC) treatment on HIV-1 infection: a double-blind placebo-controlled trial*. Eur J Clin Pharmacol 1996; 50:457-461; Witschi A, et al. *Supplementation of N-acetylcysteine fails to increase glutathione in lymphocytes and plasma of patients with AIDS*. AIDS Res Hum Retroviruses 1995; 11:141-143; de Quay B, et al. *Glutathione depletion in HIV-infected patients: role of cysteine deficiency and effect of* oral N-acetylcysteine. AIDS 1992; 6:815-819; De Rosa S C, et al. *N-acetylcysteine replenishes glutathione in HIV infection.* Eur J Clin Invest 2000; 30:915-929; Muller F, et al. *Virological and immunological effects of antioxidant treatment in patients with HIV infection.* Eur J Clin Invest 2000; 905-914; Kinscherf R, et al. *Effect of glutathione depletion and oral N-acetyl-cysteine treatment on CD4+ and CD8+ cells.* FASEB J 1994; 8:448-451; Bogden J D, et al. *Status of selected nutrients and progression of human immunodeficiency virus type 1 infection.* Am J Clin Nutr 2000; 72:809-815; Skurnick J H, et al. *Micronutrient profiles in HIV-1-infected heterosexual adults.* J Acquir Immune Defic Syndr Hum Retrovirol 1996; 12:75-83; Bogden J D, et al. *Micronutrient status and human immunodeficiency virus (HIV) infection.* Ann NY Acad Sci 1990; 587:189-195]. Due to its history of safe use as a therapeutic, NAC has been suggested as a potential supplement for glutathione replenishment in HIV since 1991 (Droge W, et al. *Modulation of lymphocyte functions and immune responses by cysteine and cysteine derivatives.* Am J Med 1991; 91:140 S-144S; Mihm S, et al. *Inhibition of HIV-1 replication and NF-kappa B activity by cysteine and cysteine derivatives.* AIDS 1991; 5:497-503; Harakeh S, and Jariwalla R J. *Comparative study of the anti-HIV activities of ascorbate and thiol-containing reducing agents in chronically HIV-infected cells.* Am J Clin Nutr 1991; 54:1231 S-1235S). While NAC has demonstrated several positive effects for people living with HIV, no research studies have reported that treatment of HIV-infected persons with NAC alone, or in combination with other nutrients or drugs, can successfully ameliorate fat maldistribution or hyperlipidemia.

Research on fatty acids in HIV has been generally limited and only one clinical trial has been reported on HIV wasting and fatty acid supplementation. A combination consisting of omega-3 fatty acids and arginine was clinically tested for its ability to affect weight gain and blood lipid levels in HIV/ART patients (Sudre, P C, et al. *A randomized double-blind controlled study of 6 months of oral nutritional supplementation with arginine and omega-3 fatty acids in HIV-infected patients.* Swiss HIV Cohort Study. AIDS 12(1)53-63). Sixty-four HIV-infected outpatients with CD4 counts greater than or equal to 100/µL were randomized to receive 7.4 g arginine plus 1.7 g omega-3 fatty acids or placebo daily. Gain in body weight and fat mass were approximately 2 and 1 kg, respectively in both treatment and placebo groups. Thus, enrichment of an oral nutritive supplement with arginine and omega-3 fatty acids did not improve weight gain or fat-free mass in HIV/ART patients. Such results imply that fatty acid supplementation alone, or in certain obvious combinations, are unlikely to positively affect fat distribution or hyperlipidemia in HIV/ART patients.

In conclusion, metabolic disorders such as hyperlipidemia and hyperglycemia are prevalent among HIV-infected individuals receiving ART. Morphological changes accompany these metabolic disorders and have been termed lipodystrophy syndrome. Affected individuals show fat redistribution, such as fat loss (e.g., in face) or fat accumulation (e.g., in abdominal area). These metabolic disorders are generally attributed to ART. Left untreated, the downstream adverse consequences of fat maldistribution include atherogenesis and atherosclerotic vascular disease. Thus, there is a critical need to provide nutritional supplementation to manage these metabolic and morphologic disorders. At this time, there are no safe and efficacious nutritional products that can normalize metabolic or body changes in HIV/ART-patients.

BRIEF SUMMARY OF THE INVENTION

The disclosed invention is directed to compositions and methods for treating, preventing or normalizing HIV/ART-associated lipoatrophy or fat maldistribution and hyperlipidemia. One embodiment of the disclosed invention consists of a conjugated fatty acid or alcohol and at least one member selected from the group consisting of thiol-containing compounds and bioavailable forms of trivalent chromium. Advantageously, the conjugated fatty acid is conjugated linoleic acid in the triglyceride form. Preferably, the thiol-containing compound is N-acetyl cysteine, lipoic acid or glutathione. Also preferably, the bioavailable form of trivalent chromium is chromium tricarnosinate. Certain compositions further comprise a conjugated fatty acid or alcohol and at least one member selected from the group consisting of thiol-containing compounds. The fatty acids and fatty alcohols herein may exist as mono-, di-, or triglycerides as well as ethers or other derivatives without loss of activity. Advantageously, the conjugated fatty acid is conjugated linoleic acid in the triglyceride form. Preferably, the thiol-containing compound is N-acetylcysteine, lipoic acid or glutathione. The compositions are useful for treating, preventing or normalizing lipoatrophy or fat maldistribution and increased serum lipids associated with anti-retroviral treatment of HIV-1 infection.

The recited compositions are incorporated into a pharmaceutically effective carrier. The pharmaceutically effective carrier may be a tablet, capsule, liquid, microbead, emulsion, powder, granule, suspension, lotion, syrup or elixir.

Embodiments of the invention provide a method of treating HIV/ART-associated fat maldistribution in a subject. The method of treatment includes administering to a subject a therapeutically effective dose of a conjugated fatty acid or conjugated fatty alcohol in combination with a pharmacologically effective dose of at least one member selected from the group consisting of a thiol-containing compound and a bioavailable form of trivalent chromium or derivates thereof. Preferably, those conjugated fatty acids or conjugated fatty alcohols include conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, docosapentaenoic acid, linoleic alcohol, linolenic alcohol, gamma linolenic alcohol, arachidonic alcohol, mead alcohol, stearidonic alcohol alpha-eleostearic alcohol, eleostearic alcohol, pinolenic alcohol, docosadienoic alcohol, docosatetraenoic alcohol, octadecadienoic alcohol, octadecatrienoic alcohol, eicosatetraenoic alcohol, eicosapentaenoic alcohol, docosahexaenoic alcohol, and docosapentaenoic alcohol. Also preferably the thiol containing compounds include cysteine, N-acetylcysteine, lipoic acid, methionine, glutathione, N-(2-mercaptopropionyl)glycine, L-2-oxothiazolidine-4-carboxylate, cysteamine, D-penicillamine, L-cysteine ethyl ester, N,N'-diacetyl-L-cystine, taurine and N-acetyl-methionine. Preferred bioavailable forms of trivalent chromium include chromium chloride, chromium carnosine, chromium picolinate, chromium carnitine, chromium nicotinate, chromium carnitinate, chromium arginate, chromium methionate, chromium dinicotinate glycine, or chromium tripicolinate.

Embodiments of the invention also provide a method of treating HIV/ART-associated hyperlipidemia in a subject. The method of treatment includes administering to a subject a therapeutically effective dose of a conjugated fatty acid or conjugated fatty alcohol and a thiol-containing compound. Preferably, those conjugated fatty acids or conjugated fatty alcohols include conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, docosapentaenoic acid, linoleic alcohol, linolenic alcohol, gamma linolenic alcohol, arachidonic alcohol, mead alcohol, stearidonic alcohol alpha-eleostearic alcohol, eleostearic alcohol, pinolenic alcohol, docosadienoic alcohol, docosatetraenoic alcohol, octadecadienoic alcohol, octadecatrienoic alcohol, eicosatetraenoic alcohol, eicosapentaenoic alcohol, docosahexaenoic alcohol, and docosapentaenoic alcohol. Also preferably the thiol containing compounds include cysteine, N-acetylcysteine, lipoic acid, methionine, glutathione, N-(2-mercaptopropionyl)glycine, L-2-oxothiazolidine-4-carboxylate, cysteamine, D-penicillamine, L-cysteine ethyl ester, N,N'-diacetyl-L-cystine, taurine and N-acetyl-methionine.

In one aspect of the invention, the conjugated fatty acid or conjugated fatty alcohol and thiol-containing compound are administered at the rate of 0.05 to 20 g per day. When comprising the composition, the bioavailable form of trivalent chromium is administered at the rate of 25 to 2,000 μg per day. Preferably, the conjugated fatty acid or conjugated fatty alcohol and thiol-containing compound are administered at the rate of 0.1 to 10 g per day and the bioavailable form of trivalent chromium is administered at the rate of 100 to 300 μg per day. Most preferably, the conjugated fatty acid or conjugated fatty alcohol and thiol-containing compound are administered at the rate of 0.5 to 6 g per day and the bioavailable form of trivalent chromium is administered at the rate of 200 μg per day.

DETAILED DESCRIPTION OF THE INVENTION

Before the present composition and methods of making and using thereof are disclosed and described, it is to be understood that the terminology used in the description presented herein is not intended to be interpreted in any limited or restrictive manner, simply because it is being utilized in conjunction with a detailed description of certain specific embodiments of the invention. It is also to be understood that this invention is not limited to the particular configurations, process steps and materials disclosed herein as such configurations, process steps and materials may vary somewhat. Furthermore, embodiments of the invention may include several novel features, no single one of which is solely responsible for its desirable attributes or which is essential to practicing the invention herein described.

It must be noted, as used in this specification and the appended claims, the singular forms "a," "an," and "the" include plural references unless the context clearly dictates otherwise.

Preferred embodiments provide compositions and methods for treating, preventing or normalizing fat maldistribution resulting from anti-retroviral therapy of HIV-1 infection. The compositions comprise as a first component, an active ingredient selected from the group consisting of conjugated fatty acids or fatty alcohols and at least one member selected from the group consisting of thiol-containing compounds and bioavailable forms of trivalent chromium. There are also provided methods of synergistically treating HIV/ART-induced fat maldistribution comprising administration of a pharmacologically effective dose of the preferred embodiments. The compositions provided by the preferred embodiments can be formulated as a dietary supplement or therapeutic composition. Dosage of the compositions of the preferred embodiments would be daily throughout the life of the subject. The compositions function to reduce or normalize visceral fat deposition and to increase subcutaneous fat deposition.

Further preferred embodiments provide compositions and methods for treating, preventing or normalizing fat maldistribution and hyperlipidemia resulting from HIV/ART. The compositions comprise as a first component, an active ingredient selected from the group of conjugated fatty acids or fatty alcohols and at least one member selected from the group consisting of a thiol-containing compounds. There are also provided methods of synergistically treating HIV/ART-induced fat maldistribution and hyperlipidemia comprising administration of a pharmacologically effective dose of the preferred embodiments. The compositions provided by the preferred embodiments can be formulated as a dietary supplement or therapeutic composition. Dosage of the compositions of the preferred embodiments would be daily throughout the life of the subject. The compositions functions to reduce or normalize visceral fat deposition, increase subcutaneous fat deposition and decrease serum lipids.

As used herein, the term "dietary supplement" refers to compositions consumed to affect structural or functional changes in physiology. The term "therapeutic composition" refers to any compounds administered to treat or prevent a disease.

As used herein, the term "HIV/ART-related lipodystrophy" refers to a mixture of central or visceral fat accumulation and peripheral or subcutaneous fat loss including hyperinsulinemia (fasting insulin >17 IU/mL) and hyperglycemia (fasting glucose >125 mg/dL) that occurs following treatment with anti-retroviral therapies.

As used herein, the term "anti-retroviral therapies" (ART) refers to all therapeutic agents used to affect the replication of the HIV-1 retrovirus irrespective of their site of action (e.g. HIV-1 reverse transcriptase and protease inhibitors).

As used herein, the term "hyperlipidemia" refers to a pathognomic condition manifest by elevated serum concentrations of total cholesterol (>200 mg/dL), LDL cholesterol (>130 mg/dL), or triglycerides (>150 mg/dL) or decreased HDL cholesterol (<40 mg/dL). Further, as used herein, the term 'fat' refers to serum and adipose triglyceride content and "triglycerides" refers to triacylglycerol esters of fatty acids.

According to the present invention, it is understood that the fatty acids and fatty alcohols described herein may exist as mono-, di- or triglycerides as well as eithers or other derivatives without loss of activity. Such other derivative may include a covalent bonding to compounds selected from the group consisting of mono- or disaccharides, amino acids, peptides, polypeptides, sulfates, amines, succinates, and acetates. Similarly, the thiols described herein may exist as covalently bonded derivatives of mono- or disaccharides, amino acids, peptides, polypeptides, sulfates, amines, succinates, and acetates. Mono- and disaccharides may be selected from the group consisting of glucose, mannose, ribose, galactose, rhamnose, arabinose, maltose, fructose, sucrose, and maltodextran.

Conjugated Fatty Acids or Conjugated Fatty Alcohols

Conjugated linoleic acid (CLA) is a nonessential fatty acid consisting of approximately 20 closely related fatty acid isomers. CLA refers to a group of polyunsaturated fatty acids that exist as positional and stero-isomers of conjugated dienoic octadecadienoate (18:2). The predominant geometric isomer in foods is the c9t11-CLA isomer followed by t7,c9-CLA, 11,13-CLA (c/t), 8,10-CLA (c/t) and the t10c12-CLA isomer. The three-dimensional stereo-isomeric configuration of CLA may be in combinations of cis or trans configurations. As used herein, the term "CLA isomers" refers to fatty acids (or alcohols) with the same 18-carbon, polyunsaturated structure. In the case of CLA, each isomer is derived from the 18-carbon essential polyunsaturated fat linoleic acid (18:2n-

6), which has two cis-double bonds at carbons 9 and 12. CLA isomers also have two double bonds, but they are adjacent to one another, or conjugated, on carbons 7 to 13, and can be cis or trans.

The term "conjugated compound" refers to a compound having at least a portion that is a hydrocarbon, with at least three consecutive carbon-carbon bonds, such that single and double carbon-carbon bonds are found in an alternating manner. Thus, the compound will include the subunit —HC=CH—H$_2$C=CH—. Two preferred categories of conjugated compounds are fatty acids and fatty alcohols. It should be noted that these di- or poly-unsaturated compounds are referred to herein using the common names of the corresponding naturally occurring compounds having the same number of carbons and unsaturations. Although such naturally occurring compounds are not necessarily conjugated, due to the arrangement of their carbon-carbon double bonds, it will be understood in the context of the present invention that only conjugated versions of those compounds are contemplated; i.e., the arrangement of the double bounds will be such that they contain the substructure —C=C—C=C—. While compounds having as few as 4, 5, 6, or 7 carbon atoms are contemplated, the preferred conjugated compounds have 8, 9, 10, 12, 14, 16 or more carbon atoms, preferably not more than 32, 30, 28, or 26 carbon atoms.

It should be noted that the phrase "conjugated fatty acid" or "conjugated fatty alcohol", as used herein, also includes isomers of fatty acids and fatty alcohols, as well as any other polyunsaturated compounds that act synergistically with sulfur-containing compounds and trivalent chromium complexes to promote fat maldistribution and decrease serum lipids in HIV/ART subjects. Suitable conjugated fatty acids include, without limitation, conjugated versions of linoleic acid, linolenic acid, gamma linolenic acid, arachidonic acid, mead acid, stearidonic acid, alpha-eleostearic acid, eleostearic acid, pinolenic acid, docosatetraenoic acid, 9,12-octadecadienoic acid, octadecatrienoic acid, eicosatetraenoic acid, eicosapentaenoic acid, docosahexaenoic acid, docosapentaenoic acid, and all other diunsaturated and polyunsaturated fatty acids. In a preferred embodiment, the conjugated fatty acid is CLA in the triglyceride form.

As used herein, the phrase "conjugated fatty alcohols" includes, without limitation, conjugated versions of linoleic alcohol, linolenic alcohol, gamma linolenic alcohol, arachidonic alcohol, mead alcohol, stearidonic alcohol alpha-eleostearic alcohol, eleostearic alcohol, pinolenic alcohol, docosadienoic alcohol, docosatetraenoic alcohol, octadecadienoic alcohol, octadecatrienoic alcohol, eicosatetraenoic alcohol, eicosapentaenoic alcohol, docosahexaenoic alcohol, docosapentaenoic alcohol, and all other diunsaturated and polyunsaturated fatty alcohols. The present invention further includes the use of other conjugated compounds having at least 4, 5, 6, 7, or 8 carbon atoms, that function synergistically with at least one sulfur-containing compound and at least one form of trivalent chromium to promote visceral fat loss, enhance subcutaneous fat deposition, and decrease serum lipids in HIV/ART. Note that the present invention includes alcohols and acids in which one or more of the double bonds result in a cis isomer, as well as those in which one or more of the double bonds result in a trans isomer. In some cases, all the double bonds are cis, while in they are all trans, and in still other cases, they are mixed cis and trans compounds.

CLA occurs naturally in the milk and fat of ruminants. In cattle, CLA is synthesized from dietary linoleic acid by symbiotic bacteria in the bovine rumen. CLA can also be made from linoleic acid during food processing, including cheese-making, deep frying and the manufacture of hydrogenated vegetable oils. However, the majority of CLA in the diet comes from dairy products. CLA supplements are generally produced from linoleic acid from sunflower, soybean and safflower oil. Commercially, CLA may be purchased from Loders Croklaan Lipid Nutrition of Channahon, Ill.

Thiol Compounds

NAC is a metabolite of cysteine, which is classified as a conditionally essential amino acid. Unlike cysteine, NAC is not found in foods but serves as a delivery form of cysteine. The acetyl-substituted amino group of NAC makes the molecule more stable against oxidation than cysteine alone and more bioavailable. As a source of thiol (S—) groups, NAC is converted in the body into metabolites capable of stimulating glutathione (GSH) synthesis, promoting detoxification, and acting directly as a free radical scavenger.

There are no known contraindications to NAC used for nutritional supplementation. Gastrointestinal distress is the most common complaint with oral NAC supplementation; this is generally manifest as nausea, vomiting and diarrhea. Other reactions reported with NAC are general and include headache, and rashes. Rarely, cysteine renal stones will occur (Kelly G S. *Clinical applications of N-acetylcysteine*. Altern Med Rev 1998; 3:114-127).

alpha-Lipoic acid (ALA), also known as thioctic acid, is a disulfide compound that is a cofactor in ATP-generating reactions in the mitochondria. It is synthesized endogenously in the mitochondria from octanoic acid and L-cysteine. Metabolic reactions in which ALA participates occur in the mitochondria and include the oxidation of pyruvic acid and the oxidation of alpha-ketoglutarate. It is also a cofactor for the oxidation of branched-chain amino acids (leucine, isoleucine and valine) via the branched-chain alpha-keto acid dehydrogenase enzyme complex.

ALA is both a dietary supplement and a drug. Branded products are available in US drug and discount stores, while in Germany ALA is classified as a drug that is approved to treat diabetic polyneuropathy and liver disorders. As a drug, ALA is manufactured for oral and parenteral use. In the treatment of diabetic neuropathy, 300 mg ALA are taken daily in divided doses.

HIV-patients use ALA generally: (1) to protect the liver, (2) to treat peripheral neuropathy, (3) to treat lipodystrophy, and (4) to slow down HIV replication (Jain, R G. et al. *Metabolic complications associated with antiretroviral therapy.* 2001 Antiviral Res 51(3), 151-77). There exists clinical data to support the use of ALA to treat various forms of liver damage (Brinkmann, W. et al. [*Is the rebound effect in liver diseases following glucocorticoid therapy avoidable by using alpha-lipoic acid?*]. 1971 Ther Ggw 110(12); Bustamante, J. et al. *Alpha-lipoic acid in liver metabolism and disease.* 1998 Free Radic Biol Med 24(6), 1023-39) and glucose utilization in diabetes (Strokov, I, et al. *The function of endogenous protective systems in patients with insulin-dependent diabetes mellitus and polyneuropathy: effect of antioxidant therapy.* 2000 Bull Exp Biol Med 130(10), 986-90). However, no studies have been performed in HIV-patients for these indications. The use of ALA for lipodystrophy and HIV replication have no published clinical support (Patrick, L. *Nutrients and HIV: part three—N-acetylcysteine, alpha-lipoic acid, L-glutamine, and L-carnitine.* 2000 Altern Med Rev 5(4), 290-305). Based upon its known metabolic actions and published clinical trials, it is unlikely that ALA could function independently to affect fat maldistribution or hyperlipidemia in HIV/ART.

There are no known contraindications to ALA used as a supplement. Formal drug interaction studies have not been performed. Based upon pharmacological studies, there was some concern that ALA might potentiate the effects of insulin. However, this potentiation of insulin has not been noted in clinical trials lasting as long as six months with doses of 1800 mg ALA daily (Ziegler, D. et al. *Treatment of symptomatic diabetic polyneuropathy with the antioxidant alpha-lipoic acid: a 7-month multicenter randomized controlled trial (ALADIN III Study). ALADIN III Study Group. Alpha-Lipoic Acid in Diabetic Neuropathy.* 1999 Diabetes Care 22(8), 1296-301).

It is believed that most of the physiological effects of ALA are due to its antioxidant activity. In the recycling of GSH, ALA functions mimic those of NAC as increasing GSH concentrations. Overall, ALA effects parallel those of NAC quite closely, with ALA exhibiting a greater potency in the ability to protect the liver, inhibit HIV replication and increase GSH concentrations.

Neither NAC, ALA nor any other thiol-containing compound has ever been reported to effectively modify fat maldistribution or reduce elevated serum lipids resulting from HIV/ART.

Preferred thiol compounds for combinations with conjugated fatty acids or conjugated fatty alcohols in the present invention include cysteine, N-acetylcysteine, lipoic acid, methionine, glutathione, N-(2-mercaptopropionyl)glycine, L-2-oxothiazolidine-4-carboxylate, cysteamine, D-penicillamine, L-cysteine ethyl ester, N,N'-diacetyl-L-cystine, taurine and N-acetyl-methionine. These compounds may be purchased commercially from Sigma (St. Louis, Mo.) or Garden State Nutritionals (West Caldwell, N.J.).

Bioavailable Trivalent Chromium

The mineral element chromium is viewed with mixed opinions. Although chromium is accepted as nutritionally essential for animals and humans, an understanding of the mechanism of its biological action and the amount of chromium needed for health and optimal function remains elusive. Because there are insufficient appropriate biochemical measures of chromium nutritional status and of the content and the bioavailability of chromium from food, there is a paucity of information that describes who would benefit from increased dietary chromium.

Chromium has been sold as a "fat burner" and is said to help build muscle tissue. However, studies evaluating its effects on weight loss are mostly negative (Grant, K E, et al. *Chromium and exercise training: effect on obese women.* 1997 Med Sci Sports Exerc 29:992-998; Trent, L K, and Thieding-Cancel D. *Effects of chromium picolinate on body composition.* 1995 J Sports Med Phys Fitness 35:273-280; Clarkson, S P, *Effects of exercise on chromium levels. Is supplementation required?* 1997 Sports Med. 23:341-349). Additional studies evaluating its benefits as a performance enhancer or aid to bodybuilding have yielded almost entirely negative results (Clarkson, P M, Effects of exercise on chromium levels. *Is supplementation required?* 1997 Sports Med 23:341-349; Joseph, L J O, et al. *Effect of resistance training with or without chromium picolinate supplementation on glucose metabolism in older men and women.* 1999 Metabolism 48:546-553; Lefavi, R G, et al. *Efficacy of chromium supplementation in athletes: emphasis on anabolism.* 1992 Int J Sport Nutr 2:111-122; Clancy, S P et al. *Effects of chromium picolinate supplementation on body composition, strength, and urinary chromium loss in football players.* 1994 Int J Sport Nutr 4:142-153; Hallmark, M A et al. *Effects of chromium and resistive training on muscle strength and body composition.* 1996 Med Sci Sports Exerc 28:139-144). Weak and contradictory evidence suggests that chromium may lower cholesterol and triglyceride levels (Mertz, W. *Chromium in human nutrition: a review.* 1993 J. Nutr 123:626-633; Press, R I, et al. *The effect of chromium picolinate on serum cholesterol and apolipoprotein fractions in human subjects.* 1990 West J Med. 152:41-45). Thus, chromium per se does not promote beneficial changes in body composition in humans. The US Federal Trade Commission emphasized this conclusion by ruling in July 1997 (United States of America before Federal Trade Commission, Docket No. C-3758) that there is no basis for claims that the trivalent form of chromium as chromium picolinate promotes weight loss and fat loss in humans.

Prior art reveals a complex composition containing chromium is proposed for the treatment of lipodystrophy syndrome. U.S. Pat. No. 6,365,176 describes a nutritional supplement for lipodystrophy in patients with type 2 diabetes mellitus. The supplement comprises a low-glycemic index carbohydrate source, a source of protein, a source of fat, a source of sterol and/or stanol, a source of chromium, a source of salicylic acid and a source of ginseng. Additionally, the composition may further comprise from about 0.1 to 20 g of N-acetylcysteine. In one embodiment, it is proposed that the nutritional supplement can be administered to HIV-infected individuals to prevent and/or treat metabolic disorders associated with lipodystrophy, such as insulin resistance, atherogenesis and cardiovascular disease as well as fat redistribution. Moreover, U.S. Pat. No. 6,365,176 teaches that the use of chromium and N-acetylcysteine in combination with a sterol or stanol, salicylic acid and ginseng are necessary for the treatment of fat maldistribution or hyperlipidemia in HIV/ART persons. Since sterols or stanols reduce serum cholesterol by interfering with the absorption of dietary cholesterol, they may also negatively affect the absorption of ART, which are for the most part fat-soluble compounds. Such combinations would be contraindicated in HIV/ART.

Additional prior art discloses the use of combinations of chromium and CLAs for type 2 diabetes, improving insulin sensitivity, reducing hypercholesterolemia and reducing body fat. McCarty suggests the use of bioactive chromium for skeletal muscle insulin resistance and CLA for adipocyte insulin resistance (McCarty, M F, *Toward a wholly nutritional therapy for type 2 diabetes.* 2000 Med Hypothesis 54(3):483-487). Similarly, U.S. patent application Ser. No. 09/957,876 filed Sep. 20, 2001 proposes methods and compositions for the treatment of diabetes, improvement of insulin sensitivity, weight loss, reduction of body fat, as well as reduction of hyperglycemia and hypercholesterolemia. The compositions include a chromium complex and a conjugated fatty acid or conjugated fatty alcohol. Both of these disclosures differ from the present invention in that the compositions provided herein do not function to reduce body weight or indiscriminately reduce body fat. Since wasting, or loss of body weight, is a constant concern in HIV patients, formulations that would cause a loss of body weight would be contraindicated. Further, the process of reversing fat maldistribution as seen in HIV/ART requires subcutaneous fat deposition in concert with visceral fat loss—a process not consistent with general fat loss. With respect to the composition, 09/957,876 does not include mono-, di-, or triglycerides of the fatty acids as described herein. Finally, the compositions of the present invention are directed to methods for the treatment of a disorder resulting from the interaction of an infectious agent and therapy against that infectious agent.

The preferred embodiments provide compositions and methods to promote fat redistribution or decrease serum lipids in HIV/ART subjects. In one embodiment, the composition comprises a composition comprising a first component selected from the group consisting of conjugated fatty acids and conjugated fatty alcohols and at least one member selected from the group consisting of thiol compounds and bioavailable trivalent chromium compounds. Preferably, the conjugated fatty acid is conjugated linoleic acid. More preferably, the conjugated linoleic acid isomers c9,t11 and t10,c12 exists in a 50:50 ratio. Preferred components from the thiol group of compounds include N-acetylcysteine, lipoic acid, taurine, N-acetylmethionine or glutathione, while preferred components of the bioavailable, trivalent chromium compounds are chromium tricarnosinate, chromium carnitine, and chromium dinicotinate glycine. Most preferably, the thiol compound is N-acetylcysteine or lipoic acid. Most preferred component of the bioavailable, trivalent chromium compounds is chromium tricarnosinate.

Another embodiment provides as a first component a conjugated fatty acid or alcohol as a second component a thiol-containing compound. There are also provided methods of promoting the normalization of fat distribution or decreasing serum lipids in HIV/ART persons comprising administration of compositions of the preferred embodiments. More preferably, the conjugated fatty acid is conjugated linoleic acid. Most preferably, the conjugated linoleic acid isomers c9,t11 and t10,c12 exists in a 50:50 ratio. Also preferably, the thiol compound is N-acetylcysteine, lipoic acid, taurine, N-acetylmethionine or glutathione. Most preferably, the thiol compound is N-acetylcysteine or lipoic acid.

The selected dosage level will depend upon activity of the particular composition, the route of administration, the severity of the condition being treated or prevented, and the condition and prior medical history of the patient being treated. However, it is within the skill of the art to start doses of the composition at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including body weight, general health, diet, time and route of administration, combination with other compositions and the severity of the particular condition being treated or prevented.

Preferably, a daily dose of the present composition would be formulated to deliver about 0.05 to 20,000 mg of conjugated fatty acids or conjugated fatty alcohols per day. More preferably, an effective daily dose of the present composition would be formulated to deliver about 1,000 to 10,000 mg of conjugated fatty acids or conjugated fatty alcohols per day. Preferably, the effective daily dose is administered once or twice a day.

A certain embodiment provides a composition comprising about 0.05 to 20,000 mg of conjugated fatty acids or conjugated fatty alcohols per day and about 0.05 to 20,000 mg thiol per day. More preferably, an effective daily dose of this embodiment would provide 1 to 10 g of both the conjugated fatty acid or conjugated fatty alcohol and the thiol-containing compound. Preferably, the ratio of the thiol-containing compound to the conjugated fatty acid or conjugated fatty alcohol is from 0.0025:1 to 40:1 (w/w). More preferably, the ratio of the thiol-containing compound to the conjugated fatty acid or conjugated fatty alcohol is 1:10 (w/w). Preferably, the effective daily dose is administered once or twice a day.

Another certain embodiment provides a composition comprising about 0.05 to 20 g of conjugated fatty acids or conjugated fatty alcohols per day, about 0.05 to 20 g thiol per day, and about 0.025 to 2 mg of bioavailable, trivalent chromium per day. In the preferred embodiment, the thiol component is decreased from 0.25 to 1.25 mg for every µg of bioavailable, trivalent chromium added. Preferably, the ratio of the conjugated fatty acid or conjugated fatty alcohols to bioavailable, trivalent chromium compound is in the range of 1:25 to 1:800,000 (w/w). More preferably, the ratio of the conjugated fatty acid or conjugated fatty alcohols to bioavailable, trivalent chromium compound (w/w) is 1:45,000 (w/w).

Yet, another certain embodiment provides a composition comprising about 0.05 to 20 g of conjugated fatty acids or conjugated fatty alcohols per day and about 0.025 to 2 mg of bioavailable, trivalent chromium per day. Preferably, the ratio of the conjugated fatty acid or conjugated fatty alcohols to bioavailable, trivalent chromium compound is in the range of 1:25 to 1:800,000 (w/w). More preferably, the ratio of the conjugated fatty acid or conjugated fatty alcohols to bioavailable, trivalent chromium compound (w/w) is 1:45,000 (w/w).

The preferred embodiments include delivering an effective amount of conjugated fatty acids or conjugated fatty alcohols. The preferred conjugated fatty acid is a member selected from the group consisting of linoleic acid (c9,t11), linoleic acid (t10,c12), alpha-linolenic acid, gamma-linolenic acid, arachidonic acid, mead acid, stearidonic acid, alpha-eleostearic acid, eleostearic acid, pinolenic acid, docosadienoic acid, docosatetraenoic acid, octadecadienoic acid, octadecatrienoic acid, eicosatetraenoic acid, eicosapentaenoic acid, docosahexaenoic acid, docosapentaenoic acid, linolic acid, and dihomo-gamma-linoleic acid. Preferred members of the group of conjugated fatty alcohols include linoleic alcohol, linolenic alcohol, gamma-linolenic alcohol, arachidonic alcohol, mead alcohol, stearidonic alcohol, alpha-eleostearic alcohol, eleostearic alcohol, pinolenic alcohol, docosadienoic alcohol, docosatetraenoic alcohol, octadecadienoic alcohol, eicosatetraenoic alcohol, eicosapentaenoic alcohol, docosahexaenoic alcohol, and docosapentaenoic alcohol. Of the species listed, those containing two asterisks (**) are particularly preferred. Commercially, the most preferred conjugated fatty acids are available from Loders Croklaan Lipid Nutrition of Channahon, Ill.

The preferred thiol source is a member selected from the group consisting of cysteine, N-acetylcysteine, lipoic acid, methionine, glutathione, N-(2-mercaptopropionyl) glycine, L-2-oxothiazolidine-4-carboxylate, cysteamine, D-penicillamine, L-cysteine ethyl ester, N,N'-Diacetyl-L-cystine, taurine and N-acetyl-methionine. Of the species listed, those containing two asterisks (**) are particularly preferred. Commercially, thiol-compounds are available from Sigma (St. Louis, Mo.).

The preferred bioavailable, trivalent chromium source is a member selected from the group consisting of chromium chloride, chromium carnosine**, chromium picolinate, chromium carnitine*, chromium nicotinate*, chromium carnitinate, chromium arginate, chromium methionate, chromium dinicotinate glycine*, or chromium tripicolinate. Of the species listed, those containing at least one asterisk (*) are preferred and those containing two asterisks (**) are particularly preferred. Commercially, bioavailable trivalent forms of chromium are available from FutureCeuticals of Santa Rosa, Calif.

Preferably, a daily dose of the present composition would be formulated to deliver about 0.05 to 20 g of conjugated fatty acids or conjugated fatty alcohols per day, about 0.05 to 20 g thiol per day, and about 0.025 to 2 mg of bioavailable, trivalent chromium per day.

More preferably, an effective daily dose of the present composition would be formulated to deliver about 0.5 to 15 g of conjugated fatty acids or conjugated fatty alcohols per day, about 0.5 to 15 g thiol per day, and about 0.1 to 1 mg of bioavailable, trivalent chromium per day. Most preferably, an effective daily dose of the present composition would be formulated to deliver about 1 to 10 g of conjugated fatty acids or conjugated fatty alcohols per day, about 1 to 10 g thiol per day, and about 0.2 to 0.6 mg of bioavailable, trivalent chromium per day.

In embodiments comprising a first component selected from the group consisting of conjugated fatty acids or conjugated fatty alcohols and a second component selected from the group consisting of thiol-containing compounds, a synergistic effect for normalizing fat distribution and decreasing adverse reactions due to thiol-containing compounds can be provided with the addition of a component consisting of a bioavailable, trivalent chromium compound. In the preferred embodiment, the thiol component is decreased from 0.25 to 1.25 mg for every μg of bioavailable, trivalent chromium added. Preferably, the ratio of the conjugated fatty acid or conjugated fatty alcohols to bioavailable, trivalent chromium compound is in the range of 1:25 to 1:800,000 (w/w). More preferably, the ratio of the conjugated fatty acid or conjugated fatty alcohols to the bioavailable, trivalent chromium compound (w/w) is 1:45,000 (w/w).

Another certain composition comprises a first component selected from the group consisting of conjugated fatty acids and conjugated fatty alcohols and a second component selected from the group consisting of bioavailable, trivalent chromium compounds. The composition comprises about 50 to 20,000 mg of conjugated fatty acids or conjugated fatty alcohols per day and about 0.025 to 2 mg of bioavailable, trivalent chromium per day. Preferably, the ratio of the conjugated fatty acid or conjugated fatty alcohols to bioavailable, trivalent chromium compound is in the range of 1:25 to 1:800,000 (w/w). More preferably, the ratio of the conjugated fatty acid or conjugated fatty alcohols to bioavailable, trivalent chromium compound (w/w) is 1:45,000 (w/w).

Further Ingredients

The formulation can also contain other ingredients such as one or a combination of other vitamins, minerals, antioxidants, fiber and, other nutritional supplements. Selection of one or several of these ingredients is a matter of formulation design, consumer and end-user preference. The amount of these ingredients added to the nutritional supplements of this invention are readily known to the skilled artisan and guidance to such amounts can be provided by the RDA and DRI (Dietary Reference Intake) doses for children and adults. Vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacin amide; zinc sulfate or oxide; calcium pantothenate; copper gluconate; riboflavin; beta-carotene; pyridoxine hydrochloride; thiamin mononitrate; folic acid; biotin; potassium iodide; selenium; sodium selenate; sodium molybdate; phylloquinone; Vitamin $D_3$; cyanocobalamin; sodium selenite; copper sulfate; Vitamin A; Vitamin E; vitamin $B_6$ and hydrochloride thereof; Vitamin C; inositol; Vitamin $B_{12}$; and potassium iodide.

The amount of other additives per unit serving are a matter of design and will depend upon the total number of unit servings of the nutritional supplement daily administered to the patient. The total amount of other ingredients will also depend, in part, upon the condition of the patient. Preferably, the amount of other ingredients will be a fraction or multiplier of the RDA or DRI amounts. For example, the nutritional supplement will comprise 50% RDI (Reference Daily Intake) of vitamins and minerals per unit dosage and the patient will consume two units per day.

Flavors, coloring agents, spices, nuts and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the nutritional supplement contains berry or other fruit flavor. The food compositions may further be coated, for example with a yogurt coating if it is as a bar.

Emulsifiers may be added for stability of the final product. Examples of suitable emulsifiers include, but are not limited to, lecithin (e.g., from egg or soy), or mono- and di-glycerides. Other emulsifiers are readily apparent to the skilled artisan and selection of suitable emulsifier(s) will depend, in part, upon the formulation and final product.

Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutritional supplement can contain natural or artificial sweeteners, e.g., glucose, sucrose, fructose, saccharides, cyclamates, aspartamine, sucralose, aspartame, acesulfame K, or sorbitol.

Manufacture of the Preferred Embodiments

The nutritional supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, soda, starch, vegetable oils, salt solutions, hydroxymethyl cellulose, carbohydrate. In a preferred embodiment, the nutritional supplements may be formulated as powders, for example, for mixing with consumable liquids, such as milk, juice, sodas, water or consumable gels or syrups for mixing into other nutritional liquids or foods. The nutritional supplements of this invention may be formulated with other foods or liquids to provide pre-measured supplemental foods, such as single serving beverages or bars, for example.

In a particularly preferred embodiment, the nutritional supplement will be formulated into a nutritional beverage, a form that has consumer appeal, is easy to administer and incorporate into one's daily regimen, thus increasing the chances of patient compliance. To manufacture the beverage, the ingredients are dried and made readily soluble in water. For the manufacture of other foods or beverages, the ingredients comprising the nutritional supplement of this invention can be added to traditional formulations or they can be used to replace traditional ingredients. Those skilled in food formulating will be able to design appropriate foods or beverages with the objective of this invention in mind.

The nutritional supplement can be made in a variety of forms, such as puddings, confections, (i.e., candy), nutritional beverages, ice cream, frozen confections and novelties, or non-baked, extruded food products such as bars. The preferred form is a powder to add to a beverage or a non-baked extruded nutritional bar. In another embodiment, the ingredients can be separately assembled. For example, certain of the ingredients (e.g., the conjugated fatty acids or alcohols and thiol compounds) can be assembled into a tablet or capsule using known techniques for their manufacture. The remaining ingredients can be assembled into a powder or nutritional bar. For the manufacture of a food bar, the dry ingredients are added with the liquid ingredients in a mixer and mixed until the dough phase is reached; the dough is put into an extruder and extruded; the extruded dough is cut into appropriate lengths; and the product is cooled. The two assembled forms comprise the nutritional supplement and can be packaged together or separately, such as in the form of a kit, as described below. Further, they can be administered together or separately, as desired.

Use of Preferred Embodiments

The preferred embodiments contemplate treatment of HIV/ART-associated fat maldistribution and hyperlipidemia. A pharmaceutically acceptable carrier may also be used in the present compositions and formulations.

The preferred embodiments are directed primarily to the treatment of human beings infected with the HIV-1 virus exhibiting fat maldistribution or hyperlipidemia. Administration can be by any method available to the skilled artisan, for example, by oral, transmucosal, or parenteral routes. The composition and nutritional supplements of the invention are intended to be orally administered daily. Based on the serving size of 15-20 g powder in 8 oz. water, the recommended dosage is once daily. For example, if the supplement is in the form of a beverage or food bar, then the patient would consume the composition after or during the largest meal. The recommended daily amounts of each ingredient, as described above, serve as a guideline for formulating the nutritional supplements of this invention. The actual amount of each ingredient per unit dosage will depend upon the number of units daily administered to the individual in need thereof. This is a matter of product design and is well within the skill of the nutritional supplement formulator.

The ingredients can be administered in a single formulation or they can be separately administered. For example, it may be desirable to administer the conjugated fatty acids or alcohols and thiol compounds in a form that masks their taste (e.g., capsule or pill form) rather than incorporating them into the nutritional composition itself (e.g., powder or bar). Thus, the invention also provides a pharmaceutical pack or kit comprising one or more containers filled with one or more of the ingredients of the nutritional compositions of the invention (e.g., nutritional supplement in the form of a powder and capsules containing conjugated fatty acids and thiol compounds). Optionally associated with such container(s) can be a notice in the form prescribed by a government agency regulating the manufacture, use or sale of pharmaceutical products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet.

All references cited are incorporated by reference in their entirety.

The descriptions below are of specific examples setting forth preferred embodiments and are not intended to limit the scope.

Example 1

A double-blinded, placebo-controlled study in HIV patients exhibiting HIV/ART-associated fat maldistribution is conducted. Over a 12-week period, HIV-positive subjects, (1) with a history of normal fat distribution and serum lipids prior to receiving ART and (2) with fat maldistribution and hyperlipidemia while receiving ART, are randomly assigned to one of two groups. One group is given the test material described in Table 1 and the second group receives a placebo powder of identical appearance and caloric content. The conjugated linoleic acid, as a triglyceride, is obtained from Loders Croklaan Lipid Nutrition of Channahon, Ill. and the N-acetylcysteine is purchased from Garden State Nutritionals of West Caldwell, N.J. Instructions supplied with the powders indicate that they are to be mixed with eight ounces of cold water and taken once per day. The powder is manufactured according to routine processes known in the art.

TABLE 1

Berry-flavored dietary supplement drink mix containing conjugated linoleic acid and N-acetylcysteine.

Supplement Facts
Serving Size: 1 pouch (20 g)

| | Amount Per Serving | % Daily Value |
|---|---|---|
| Calories | 102 | |
| Total carbohydrate | 6 g | 2%* |
| Sugars | 0 g | † |
| Conjugated Linoleic Acid | 6 g | † |
| N-Acetylcysteine | 6 g | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

A maximum of forty HIV-positive persons participate in this study. All patients remain on their ART. Twenty patients are randomly assigned to receive a powder drink described in Table 1 and 20 patients are randomly assigned to receive the placebo for 12 weeks. These patients are seen at baseline, at six weeks and at 12 weeks for evaluation.

Estimates of nutrient intake are made using a dietary recall form covering a one-week period. Complete blood counts, serum chemistries, serum lipids (total cholesterol, LDL cholesterol, HDL cholesterol, and triglycerides), HIV viral load, CD4, CD8, fasting blood glucose, liver function tests, morphological measurements (wrist, mid-forearm, mid-bicep, waste, thigh and hip circumference) and percent body fat using bioelectrical impedance analysis (BIA) are monitored for each subject at all three clinic visits. At both the initial visit and the 12-week visit, fat distribution is also assessed using a Computed tomography (CT) scan of the midsection and thigh. In addition, a physical examination is performed at each visit. Assessment of compliance and request for adverse reactions are made at visits two and three. Alterations of fat distribution, loss of visceral fat and gain in subcutaneous fat, are defined as the primary efficacy variables. A one- or two-tailed paired t-test is used to assess statistical significance of these variables between the test and placebo groups. Continuous variables are analyzed using analysis of variance procedures. Differences are deemed significant when the probability of a type I error is less than five percent adjusted for appropriate one- or two-tailed testing.

Significant differences are noted in fat distribution as determined by BIA and CT in the test subjects at both the six- and twelve-week examinations. Waist circumferences decrease in concert with increases in mid-forearm, mid-bicep and thigh circumferences. Body weights do not change in either group and percent body fat is not altered with the test material relative to the placebo. Serum cholesterol and triglycerides are significantly reduced in test subjects with no changes in placebo control subjects. There are no adverse effects noted as evidenced by complete blood counts, serum chemistries or physical examination.

The only untoward effect observed in the study is the lack of palatability of the formulation. Subjects note a bad aftertaste attributed to the thiol-containing component; these are also complain of stomach upset. None of the placebo subjects complains of aftertaste or stomach issues.

Thus, the 1:1 combination of N-acetylcysteine and conjugated linoleic acid used in this study effectively reverses the HIV-/ART-associated visceral fat accumulation and supports peripheral fat deposition with decreases in total percent body fat. The combination also significantly reduces serum lipids.

The following examples illustrate formulations that can be utilized in the same manner as those in Example 1 with similar results. Lipoic acid is obtained from Garden State Nutritionals (West Caldwell, N.J.).

Example 2

TABLE 2

Berry-flavored dietary supplement drink mix containing conjugated linoleic acid and N-acetylcysteine.

Supplement Facts
Serving Size: 1 pouch (20 g)

|  | Amount Per Serving | % Daily Value |
|---|---|---|
| Calories | 117 |  |
| Total carbohydrate | 6 g | 2%* |
| Sugars | 0 g | † |
| Conjugated Linoleic Acid | 10 g | † |
| N-Acetylcysteine | 750 mg | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

Example 3

TABLE 3

Berry-flavored dietary supplement drink mix containing conjugated linoleic acid and N-acetylcysteine.

Supplement Facts
Serving Size: 1 pouch (20 g)

|  | Amount Per Serving | % Daily Value |
|---|---|---|
| Calories | 117 |  |
| Total carbohydrate | 6 g | 2%* |
| Sugars | 0 g | † |
| Conjugated Linoleic Acid | 750 mg | † |
| N-Acetylcysteine | 10 g | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

Example 4

TABLE 54

Berry-flavored dietary supplement drink mix containing conjugated linoleic acid and lipoic acid.

Supplement Facts
Serving Size: 1 pouch (20 g)

|  | Amount Per Serving | % Daily Value |
|---|---|---|
| Calories | 114 |  |
| Total carbohydrate | 6 g | 2%* |
| Sugars | 0 g | † |
| Conjugated Linoleic Acid | 10 g | † |
| Lipoic Acid | 300 mg | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

Example 5

TABLE 5

Berry-flavored dietary supplement drink mix containing conjugated linoleic acid and lipoic acid.

Supplement Facts
Serving Size: 1 pouch (20 g)

|  | Amount Per Serving | % Daily Value |
|---|---|---|
| Calories | 114 |  |
| Total carbohydrate | 6 g | 2%* |
| Sugars | 0 g | † |
| Conjugated Linoleic Acid | 500 mg | † |
| Lipoic Acid | 1 g | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

All of the above examples illustrate efficacious formulations that can be utilized in the same manner as those in Example 1 with similar results, including the untoward effects of bad aftertaste and stomach upset. The following formulations, which contain a bioavailable form of trivalent chromium and reduced quantities of thiol-containing compounds, illustrate efficacious formulations that can be utilized in the same manner as those in Examples 1-5 without the untoward effects of bad aftertaste and stomach upset.

Example 6

TABLE 6

Berry-flavored dietary supplement drink mix containing conjugated chromium tricamosinate, conjugated linoleic acid and N-acetylcysteine.

Supplement Facts
Serving Size: 1 pouch (20 g)

|  | Amount Per Serving | % Daily Value |
|---|---|---|
| Calories | 80 |  |
| Total carbohydrate | 6 g | 2%* |
| Sugars | 0 g | † |

TABLE 6-continued

Berry-flavored dietary supplement drink mix
containing conjugated chromium tricarnosinate,
conjugated linoleic acid and N-acetylcysteine.

Supplement Facts
Serving Size: 1 pouch (20 g)

|  | Amount Per Serving | % Daily Value |
|---|---|---|
| Chromium (as chromium tricarnosinate) | 200 mcg | 166% |
| Conjugated Linoleic Acid | 6 g | † |
| N-Acetylcysteine | 500 mg | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

Example 7

TABLE 7

Berry-flavored dietary supplement drink mix
containing conjugated chromium tricarnosinate,
conjugated linoleic acid and lipoic acid.

Supplement Facts
Serving Size: 1 pouch (20 g)

|  | Amount Per Serving | % Daily Value |
|---|---|---|
| Calories | 78 |  |
| Total carbohydrate | 6 g | 2%* |
| Sugars | 0 g | † |
| Chromium (as chromium tricarnosinate) | 200 mcg | 166% |
| Conjugated Linoleic Acid | 6 g | † |
| Lipoic Acid | 250 mg | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

The following formulation, which contains a bioavailable form of trivalent chromium, increased quantities of conjugated fatty acids relative to the other formulations presented, and no thiol-containing compounds, illustrates a formulation that can be utilized in the same manner as those in Examples 1-7. While the formulation in Example 8 does not produce the untoward effects of bad aftertaste and stomach upset, its efficacy is limited to reversing the ART-associated visceral fat accumulation and supporting peripheral fat deposition with no change in total percent body fat. This combination does not reduce serum triglycerides nor does it affect other serum lipid components in HIV-infected persons exhibiting fat maldistribution, but does increase insulin sensitivity in concert with decreases in visceral fat noted in CT scans.

Example 8

TABLE 8

Berry-flavored dietary supplement drink mix containing
chromium tricarnosinate and conjugated linoleic acid.

Supplement Facts
Serving Size: 1 pouch (20 g)

|  | Amount Per Serving | % Daily Value |
|---|---|---|
| Calories | 78 |  |
| Total carbohydrate | 6 g | 2%* |
| Sugars | 0 g | † |

TABLE 8-continued

Berry-flavored dietary supplement drink mix containing
chromium tricarnosinate and conjugated linoleic acid.

Supplement Facts
Serving Size: 1 pouch (20 g)

|  | Amount Per Serving | % Daily Value |
|---|---|---|
| Chromium (as chromium tricarnosinate) | 200 mcg | 166% |
| Conjugated Linoleic Acid | 9 g | † |

† Daily value not established.
Percent values are based on 2,000 calorie diet.
Other ingredients would include natural flavors, malic acid, beet juice powder, citric acid, and silica. Directions for use would be to mix one serving with eight ounces of cold water. Additional directions would indicate to keep out of reach of children, store at 15-30° C. (59-86° F.), protect from heat, light and moisture, and not to purchase if the seal is broken.

Thus, among the various formulations taught there has been disclosed a formulation containing, as a first active component, a conjugated fatty acid or conjugated alcohol and, as a second component, at least one member selected from the group of thiol-containing compounds and bioavailable trivalent chromium compounds. It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, powder, lotion, food or bar manufacturing process as well as vitamins, flavorings and carriers. Other such changes or modifications would include the use of herbs or other botanical products containing the combinations of the preferred embodiments disclosed above. Many additional modifications and variations of the embodiments described herein may be made without departing from the scope, as is apparent to those skilled in the art. The specific embodiments described herein are offered by way of example only.

What is claimed is:

1. A method for treating or normalizing subcutaneous fat loss resulting from anti-retroviral treatment of HIV-1 infection in a subject in need thereof consisting of administering to said subject a composition consisting of a pharmaceutically effective dose of conjugated linoleic acid in combination with a pharmacologically effective dose of N-acetylcysteine and non-active ingredients selected from the group consisting of flavors, coloring agents, emulsifiers, preservatives and a pharmaceutically acceptable carrier.

2. A method for treating or normalizing hyperlipidemia coincident with subcutaneous fat loss and body wasting resulting from anti-retroviral treatment of HIV-1 infection in a subject in need thereof consisting of administering to said subject a composition consisting of a pharmaceutically effective dose of a conjugated linoleic acid in combination with a pharmacologically effective dose of N-acetylcysteine and non-active ingredients selected from the group consisting of flavors, coloring agents, emulsifiers, preservatives and a pharmaceutically acceptable carrier.

* * * * *